(12) United States Patent
Kirschman

(10) Patent No.: US 8,795,370 B2
(45) Date of Patent: *Aug. 5, 2014

(54) FUSION SYSTEM AND METHOD FOR FUSING SPINAL BONES

(75) Inventor: David Louis Kirschman, Dayton, OH (US)

(73) Assignee: X-spine Systems, Inc., Miamisburg, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 13/568,429

(22) Filed: Aug. 7, 2012

(65) Prior Publication Data

US 2012/0303126 A1 Nov. 29, 2012

Related U.S. Application Data

(60) Continuation of application No. 12/640,061, filed on Dec. 17, 2009, now Pat. No. 8,282,682, which is a continuation-in-part of application No. 11/624,341, filed on Jan. 18, 2007, now Pat. No. 7,655,028, which is a division of application No. 10/675,361, filed on Sep. 30, 2003, now Pat. No. 7,182,782, application No. 13/568,429, which is a continuation of application No. 10/858,629, filed on Jun. 2, 2004, now Pat. No. 7,641,701, which is a continuation-in-part of application No. 10/675,361, filed on Sep. 30, 2003, now Pat. No. 7,182,782.

(51) Int. Cl.
*A61F 2/44* (2006.01)

(52) U.S. Cl.
USPC .................................. 623/17.11; 623/17.16

(58) Field of Classification Search
CPC ........... A61B 17/7059; A61B 17/8047; A61B 17/8052; A61B 17/8042; A61F 2/44; A61F 2/4465; A61F 2310/00161; A61F 17/8605; A61F 2/30744; A61F 2002/2835; A61F 2002/30062; A61F 2002/30131
USPC ..................... 623/17.11–17.16; 606/279, 247
See application file for complete search history.

(56) References Cited

U.S. PATENT DOCUMENTS

| | | |
|---|---|---|
| 1,025,008 A | 4/1912 | Miner |
| 1,037,577 A | 9/1912 | Baker |
| 2,677,369 A | 5/1954 | Knowles |

(Continued)

FOREIGN PATENT DOCUMENTS

| | | |
|---|---|---|
| CA | 1292596 | 12/1991 |
| CA | 2133276 | 4/1995 |

(Continued)

*Primary Examiner* — Pedro Philogene
(74) *Attorney, Agent, or Firm* — Jacox, Meckstroth & Jenkins

(57) ABSTRACT

This invention relates to a spinal fusion system and method for use as a prosthetic implant. The system and method includes a housing dimensioned to be situated between adjacent spinal bones, such as adjacent vertebrae. The housing cooperates with the spinal bones to define a graft area for receiving graft material, which may be inserted anteriorly into the housing during a surgical operation such as a vertebrectomy or discectomy. A housing may have various features such as migration preventers to prevent the housing from migrating posteriorly towards a spinal column and can be used with a cover that permits the housing to "float" relative thereto. Screws are provided in one embodiment and are dimensioned or configured to lock against each other to retain the screws and, consequently, the cover in place.

55 Claims, 11 Drawing Sheets

(56) References Cited

U.S. PATENT DOCUMENTS

| | | |
|---|---|---|
| 3,848,601 A | 11/1974 | Ma et al. |
| 3,867,728 A | 2/1975 | Stubstad et al. |
| 4,157,715 A | 6/1979 | Westerhoff |
| 4,309,777 A | 1/1982 | Patil |
| 4,349,921 A | 9/1982 | Kuntz |
| 4,488,543 A | 12/1984 | Tornier |
| 4,553,273 A | 11/1985 | Wu |
| 4,599,086 A | 7/1986 | Doty |
| 4,611,581 A | 9/1986 | Steffee |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Buettner-Janz et al. |
| 4,834,757 A | 5/1989 | Brantigan |
| 4,878,915 A | 11/1989 | Brantigan |
| 4,904,261 A | 2/1990 | Dove et al. |
| 4,988,349 A | 1/1991 | Pennig |
| 4,997,432 A | 3/1991 | Keller |
| 5,041,113 A | 8/1991 | Biedermann et al. |
| 5,084,049 A | 1/1992 | Asher et al. |
| 5,085,660 A | 2/1992 | Lin |
| 5,192,327 A | 3/1993 | Brantigan |
| 5,246,443 A | 9/1993 | Mai |
| 5,261,911 A | 11/1993 | Carl |
| 5,290,312 A | 3/1994 | Kojimoto et al. |
| 5,324,290 A | 6/1994 | Zdeblick et al. |
| 5,330,473 A | 7/1994 | Howland |
| 5,364,399 A | 11/1994 | Lowery et al. |
| 5,405,391 A | 4/1995 | Hednerson et al. |
| 5,425,772 A | 6/1995 | Brantigan |
| 5,439,463 A | 8/1995 | Lin |
| 5,549,612 A | 8/1996 | Yapp et al. |
| 5,554,191 A | 9/1996 | Lahille et al. |
| 5,601,551 A | 2/1997 | Taylor et al. |
| 5,601,553 A | 2/1997 | Trebing et al. |
| 5,609,635 A * | 3/1997 | Michelson ................. 623/17.16 |
| 5,609,637 A | 3/1997 | Biedermann et al. |
| 5,616,142 A | 4/1997 | Yuan et al. |
| 5,616,144 A | 4/1997 | Yapp et al. |
| 5,620,443 A | 4/1997 | Gertzbein et al. |
| 5,672,177 A | 9/1997 | Seldin |
| 5,681,310 A | 10/1997 | Yuan et al. |
| 5,681,311 A | 10/1997 | Foley et al. |
| 5,702,395 A | 12/1997 | Hopf |
| 5,713,899 A | 2/1998 | Marnay et al. |
| 5,713,900 A | 2/1998 | Benzel et al. |
| 5,716,415 A | 2/1998 | Steffee |
| 5,720,746 A | 2/1998 | Soubeiran |
| 5,776,196 A | 7/1998 | Matsuzaki et al. |
| 5,843,082 A | 12/1998 | Yuan et al. |
| 5,876,402 A | 3/1999 | Errico et al. |
| 5,888,228 A | 3/1999 | Knothe et al. |
| 5,904,683 A | 5/1999 | Pohndorf et al. |
| 5,925,047 A | 7/1999 | Errico et al. |
| 5,951,558 A | 9/1999 | Fiz |
| 5,954,722 A | 9/1999 | Bono |
| 6,030,389 A | 2/2000 | Wagner et al. |
| 6,066,175 A | 5/2000 | Henderson et al. |
| 6,106,557 A | 8/2000 | Robioneck et al. |
| 6,136,002 A | 10/2000 | Shih et al. |
| 6,139,550 A | 10/2000 | Michelson |
| 6,152,927 A | 11/2000 | Farris et al. |
| 6,159,211 A | 12/2000 | Boriani et al. |
| 6,159,213 A | 12/2000 | Rogozinski |
| 6,159,245 A | 12/2000 | Meriwether et al. |
| 6,171,307 B1 | 1/2001 | Orlich |
| 6,193,721 B1 | 2/2001 | Michelson |
| D440,311 S | 4/2001 | Michelson |
| 6,224,602 B1 | 5/2001 | Hayes |
| 6,235,033 B1 | 5/2001 | Brace et al. |
| 6,235,034 B1 | 5/2001 | Bray |
| 6,235,059 B1 * | 5/2001 | Benezech et al. .......... 623/17.16 |
| 6,245,108 B1 | 6/2001 | Biscup |
| 6,258,089 B1 | 7/2001 | Campbell et al. |
| 6,261,291 B1 | 7/2001 | Talaber et al. |
| 6,261,586 B1 | 7/2001 | McKay |
| 6,264,655 B1 | 7/2001 | Pisharodi |
| 6,293,949 B1 | 9/2001 | Justis et al. |
| D449,692 S | 10/2001 | Michelson |
| 6,306,136 B1 | 10/2001 | Baccelli |
| 6,306,139 B1 | 10/2001 | Fuentes |
| 6,328,738 B1 | 12/2001 | Suddaby |
| 6,361,537 B1 | 3/2002 | Anderson |
| 6,368,351 B1 | 4/2002 | Glenn et al. |
| 6,371,986 B1 | 4/2002 | Bagby |
| 6,383,186 B1 | 5/2002 | Michelson |
| 6,398,783 B1 | 6/2002 | Michelson |
| 6,413,259 B1 | 7/2002 | Lyons et al. |
| 6,416,528 B1 | 7/2002 | Michelson |
| 6,428,542 B1 | 8/2002 | Michelson |
| 6,432,106 B1 | 8/2002 | Fraser |
| 6,454,769 B2 | 9/2002 | Wagner et al. |
| 6,454,771 B1 | 9/2002 | Michelson |
| 6,485,517 B1 | 11/2002 | Michelson |
| 6,503,250 B2 | 1/2003 | Paul |
| 6,527,776 B1 | 3/2003 | Michelson |
| 6,533,786 B1 | 3/2003 | Needham et al. |
| 6,558,423 B1 | 5/2003 | Michelson |
| 6,558,424 B2 | 5/2003 | Thalgott |
| 6,569,201 B2 | 5/2003 | Moumene et al. |
| 6,572,619 B2 | 6/2003 | Santilli |
| 6,575,975 B2 | 6/2003 | Brace et al. |
| 6,592,586 B1 | 7/2003 | Michelson |
| 6,599,290 B2 | 7/2003 | Bailey et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,626,907 B2 | 9/2003 | Blain et al. |
| 6,652,525 B1 | 11/2003 | Assaker et al. |
| 6,669,700 B1 | 12/2003 | Farris et al. |
| 6,676,703 B2 | 1/2004 | Biscup |
| 6,679,883 B2 | 1/2004 | Hawkes et al. |
| 6,699,249 B2 | 3/2004 | Schlapfer et al. |
| 6,712,818 B1 | 3/2004 | Michelson |
| 6,730,127 B2 | 5/2004 | Michelson |
| 6,755,833 B1 | 6/2004 | Paul et al. |
| 6,776,781 B1 | 8/2004 | Uwaydah |
| 6,776,798 B2 | 8/2004 | Camino et al. |
| 6,837,905 B1 | 1/2005 | Lieberman |
| 6,852,113 B2 | 2/2005 | Nathanson et al. |
| 6,890,334 B2 | 5/2005 | Brace et al. |
| 6,916,320 B2 | 7/2005 | Michelson |
| 6,926,737 B2 | 8/2005 | Jackson |
| 6,936,050 B2 | 8/2005 | Michelson |
| 6,936,051 B2 | 8/2005 | Michelson |
| 6,964,664 B2 | 11/2005 | Freid et al. |
| 6,969,390 B2 | 11/2005 | Michelson |
| 6,974,479 B2 | 12/2005 | Trieu |
| 7,001,387 B2 | 2/2006 | Farris et al. |
| 7,018,414 B2 | 3/2006 | Brau et al. |
| 7,033,394 B2 | 4/2006 | Michelson |
| 7,041,105 B2 | 5/2006 | Michelson |
| 7,041,135 B2 | 5/2006 | Michelson |
| 7,044,952 B2 | 5/2006 | Michelson |
| 7,060,097 B2 | 6/2006 | Fraser et al. |
| 7,074,221 B2 | 7/2006 | Michelson |
| 7,077,843 B2 | 7/2006 | Thramann et al. |
| 7,097,645 B2 | 8/2006 | Michelson |
| 7,112,202 B2 | 9/2006 | Michelson |
| 7,112,222 B2 | 9/2006 | Fraser et al. |
| 7,115,130 B2 | 10/2006 | Michelson |
| 7,118,573 B2 | 10/2006 | Michelson |
| 7,137,984 B2 | 11/2006 | Michelson |
| 7,163,561 B2 | 1/2007 | Michelson |
| 7,182,782 B2 * | 2/2007 | Kirschman ................. 623/17.11 |
| 7,186,256 B2 | 3/2007 | Michelson |
| 7,201,753 B2 | 4/2007 | Schlapfer et al. |
| 7,229,477 B2 | 6/2007 | Biscup |
| 7,232,463 B2 * | 6/2007 | Falahee ....................... 623/17.11 |
| 7,238,203 B2 | 7/2007 | Bagga et al. |
| 7,255,699 B2 | 8/2007 | Paul |

(56) References Cited

U.S. PATENT DOCUMENTS

| | | |
|---|---|---|
| 7,303,564 B2 | 12/2007 | Freid et al. |
| 7,399,301 B2 | 7/2008 | Michelson |
| 7,503,933 B2 * | 3/2009 | Michelson ............... 623/17.11 |
| 7,537,603 B2 | 5/2009 | Huebner et al. |
| 7,594,931 B2 * | 9/2009 | Louis et al. ............... 623/17.11 |
| 7,611,527 B2 | 11/2009 | Freid et al. |
| 7,637,951 B2 | 12/2009 | Michelson |
| 7,637,954 B2 | 12/2009 | Michelson |
| 7,641,701 B2 | 1/2010 | Kirschman |
| 7,662,154 B2 | 2/2010 | Ribeiro |
| 7,780,708 B2 | 8/2010 | Morris et al. |
| 7,846,190 B2 | 12/2010 | Ball |
| 7,955,362 B2 | 6/2011 | Erickson et al. |
| 8,062,367 B2 | 11/2011 | Kirschman |
| 8,088,163 B1 | 1/2012 | Kleiner |
| 8,182,539 B2 | 5/2012 | Tyber et al. |
| 8,282,682 B2 * | 10/2012 | Kirschman ............... 623/17.11 |
| 8,343,223 B2 | 1/2013 | Bucci |
| 8,372,152 B2 | 2/2013 | Kirschman |
| 2002/0004683 A1 | 1/2002 | Michelson |
| 2002/0045898 A1 | 4/2002 | Freid et al. |
| 2002/0058939 A1 | 5/2002 | Wagner et al. |
| 2002/0120273 A1 | 8/2002 | Needham et al. |
| 2002/0138146 A1 * | 9/2002 | Jackson ............... 623/17.15 |
| 2002/0143400 A1 | 10/2002 | Biscup |
| 2002/0173790 A1 | 11/2002 | Chang et al. |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023307 A1 | 1/2003 | Michelson |
| 2003/0045880 A1 | 3/2003 | Michelson |
| 2003/0060828 A1 | 3/2003 | Michelson |
| 2003/0078668 A1 | 4/2003 | Michelson |
| 2003/0093082 A1 | 5/2003 | Campbell et al. |
| 2003/0105462 A1 | 6/2003 | Haider |
| 2003/0120274 A1 | 6/2003 | Morris et al. |
| 2003/0181912 A1 | 9/2003 | Michelson |
| 2003/0187443 A1 | 10/2003 | Lauryssen et al. |
| 2003/0191471 A1 | 10/2003 | Michelson |
| 2003/0191472 A1 | 10/2003 | Michelson |
| 2003/0199876 A1 | 10/2003 | Brace et al. |
| 2003/0199983 A1 | 10/2003 | Michelson |
| 2003/0208204 A1 | 11/2003 | Bailey et al. |
| 2003/0225409 A1 | 12/2003 | Freid et al. |
| 2004/0019353 A1 | 1/2004 | Freid et al. |
| 2004/0030338 A1 | 2/2004 | Paul |
| 2004/0092939 A1 | 5/2004 | Freid et al. |
| 2004/0097934 A1 | 5/2004 | Farris et al. |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127901 A1 | 7/2004 | Huebner et al. |
| 2004/0127903 A1 | 7/2004 | Schlapfer et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMauro et al. |
| 2004/0193271 A1 | 9/2004 | Fraser et al. |
| 2004/0199254 A1 | 10/2004 | Louis et al. |
| 2004/0210313 A1 | 10/2004 | Michelson |
| 2004/0210314 A1 | 10/2004 | Michelson |
| 2004/0230309 A1 | 11/2004 | DiMauro et al. |
| 2005/0038513 A1 | 2/2005 | Michelson |
| 2005/0096657 A1 | 5/2005 | Autericque et al. |
| 2005/0187551 A1 | 8/2005 | Orbay et al. |
| 2005/0192576 A1 | 9/2005 | Michelson |
| 2005/0251137 A1 | 11/2005 | Ball |
| 2006/0195100 A1 | 8/2006 | Kirschman |
| 2007/0043366 A1 | 2/2007 | Pfefferle et al. |
| 2007/0106388 A1 | 5/2007 | Michelson |
| 2007/0123885 A1 | 5/2007 | Kirschman |
| 2007/0162013 A1 | 7/2007 | Jacene et al. |
| 2008/0021476 A1 | 1/2008 | Kirschman |
| 2008/0097444 A1 | 4/2008 | Erickson et al. |
| 2009/0036985 A1 | 2/2009 | Whiting |
| 2009/0234359 A1 | 9/2009 | Onoue et al. |
| 2010/0070037 A1 | 3/2010 | Parry et al. |
| 2010/0106249 A1 | 4/2010 | Tyber et al. |
| 2011/0015745 A1 | 1/2011 | Bucci |
| 2011/0040382 A1 | 2/2011 | Muhanna |
| 2013/0006367 A1 | 1/2013 | Bucci |

FOREIGN PATENT DOCUMENTS

| | | |
|---|---|---|
| CA | 2163243 | 9/1995 |
| CA | 2383634 | 8/2008 |
| DE | 1139331 | 11/1962 |
| DE | 4409833 | 10/1995 |
| EP | 0179695 | 4/1986 |
| EP | 0307241 | 3/1989 |
| EP | 0599640 | 6/1994 |
| EP | 1169971 | 1/2001 |
| EP | 1437105 | 7/2004 |
| FR | 2727005 | 5/1996 |
| FR | 2827150 | 1/2003 |
| GB | 0401362.9 | 1/2004 |
| WO | 89/09035 | 10/1989 |
| WO | 97/20526 | 6/1997 |
| WO | 99/63914 | 12/1999 |
| WO | 00/66044 | 11/2000 |
| WO | 00/66045 | 11/2000 |
| WO | 02/03885 | 1/2002 |
| WO | 03005939 | 1/2003 |
| WO | 2004086990 | 10/2004 |
| WO | 2005/070346 | 8/2005 |
| WO | WO2008065443 | 6/2008 |
| WO | WO2011008864 | 1/2011 |

* cited by examiner

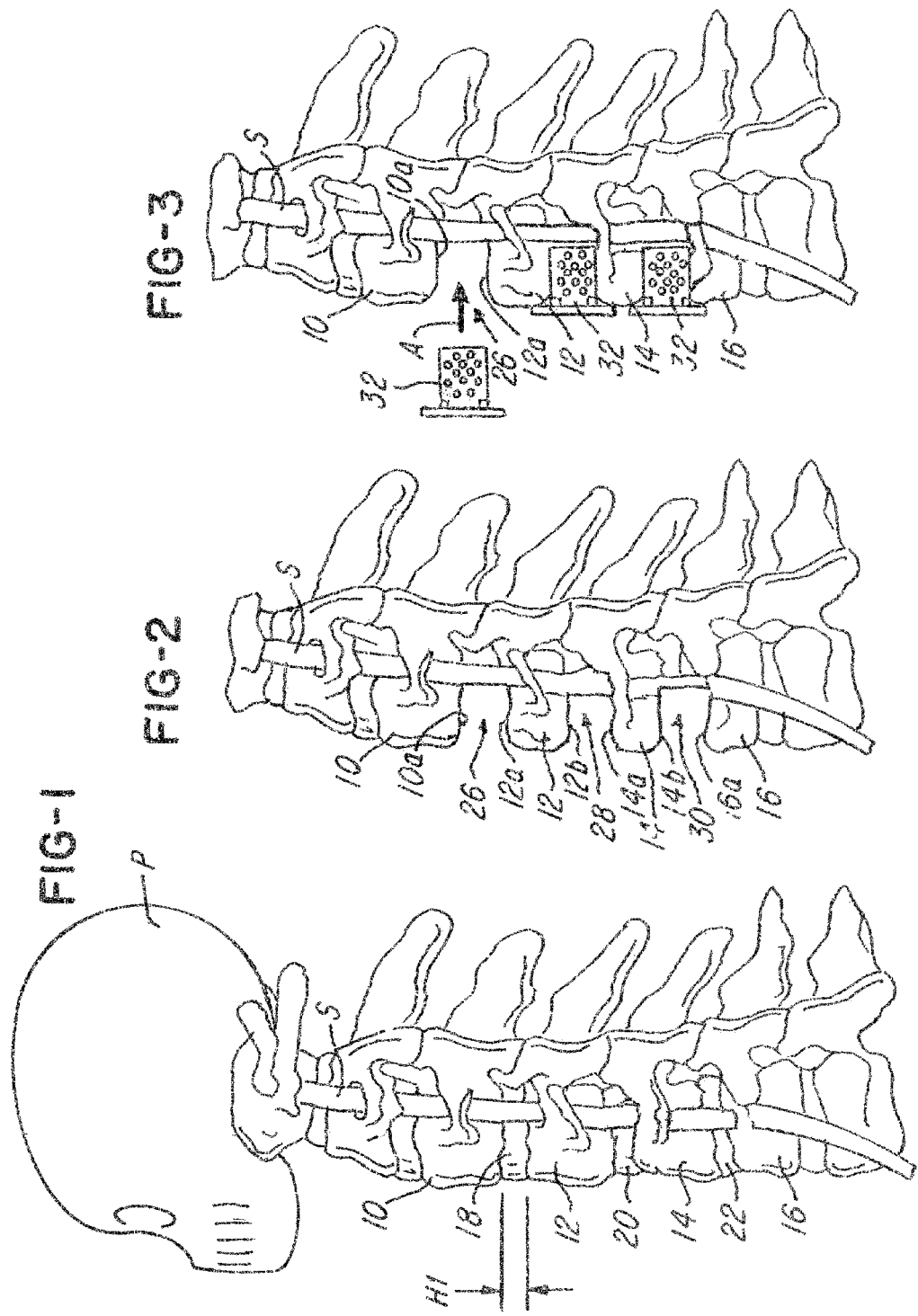

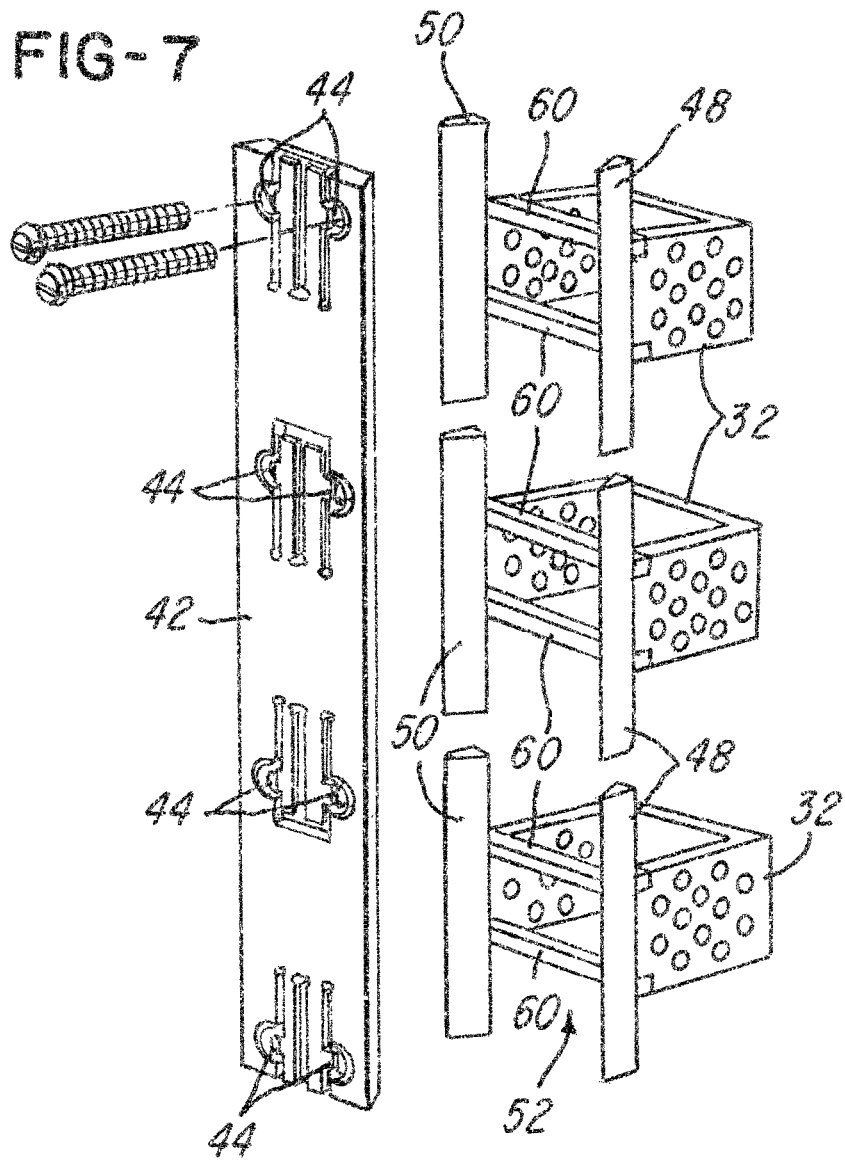

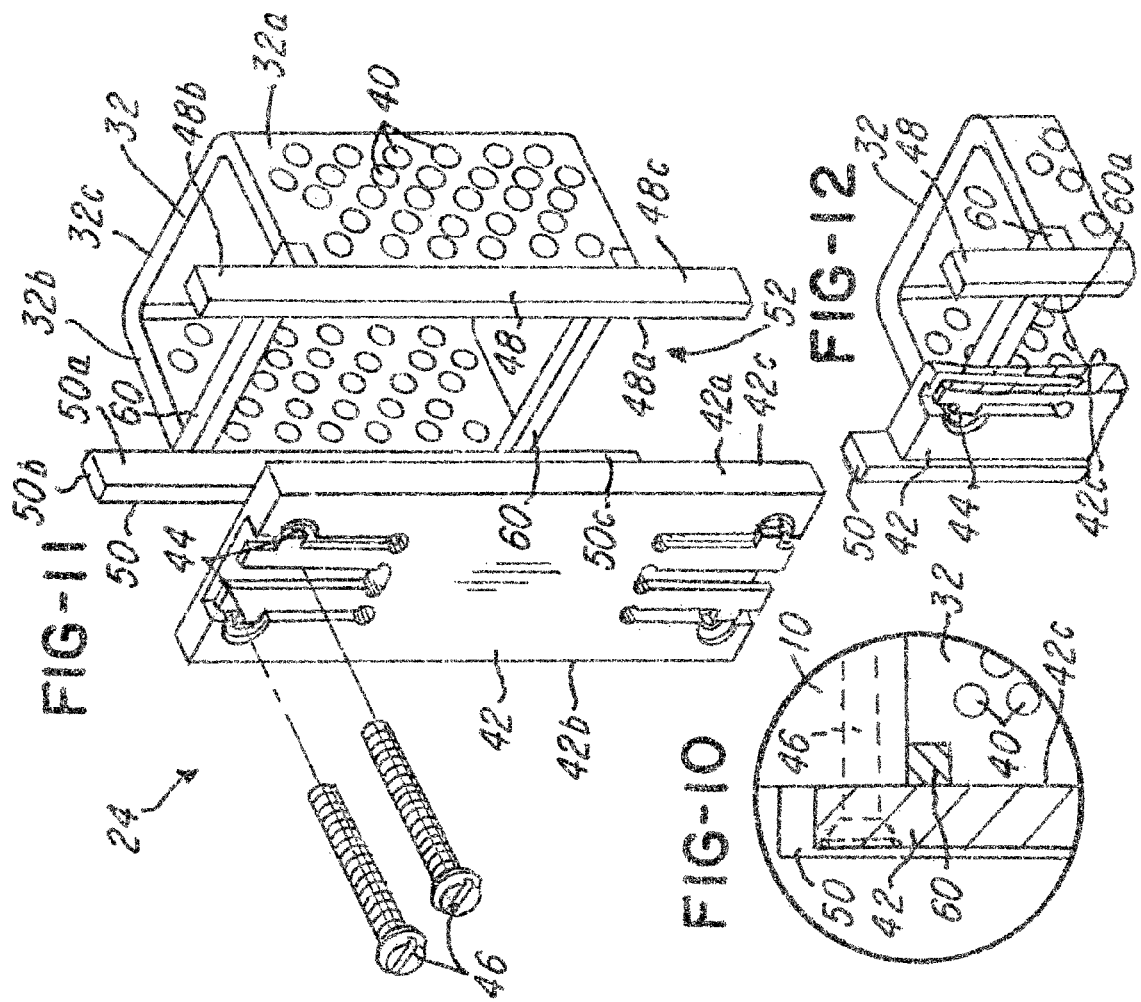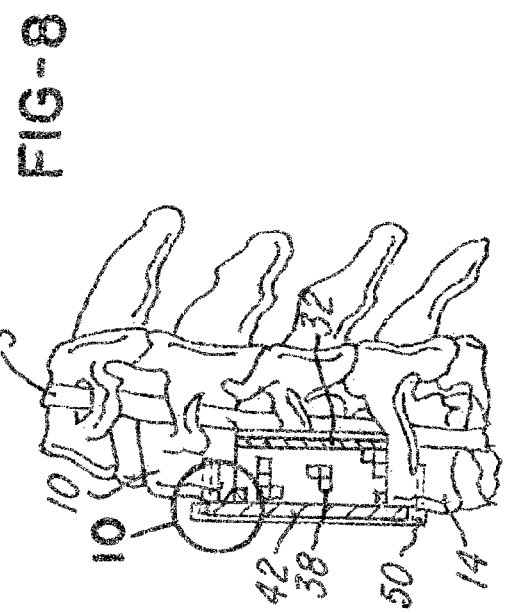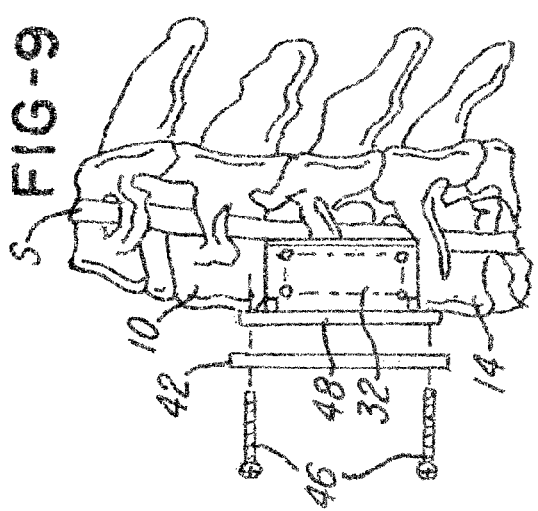

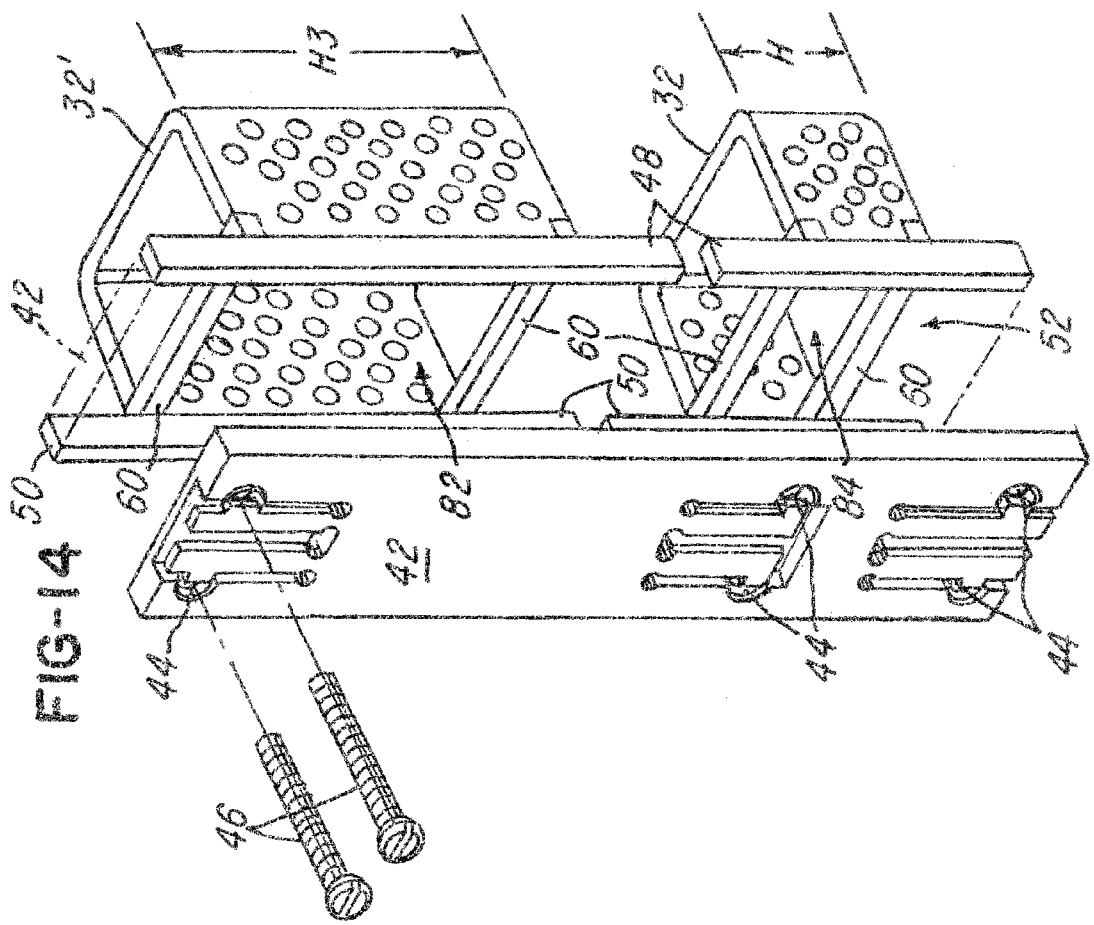
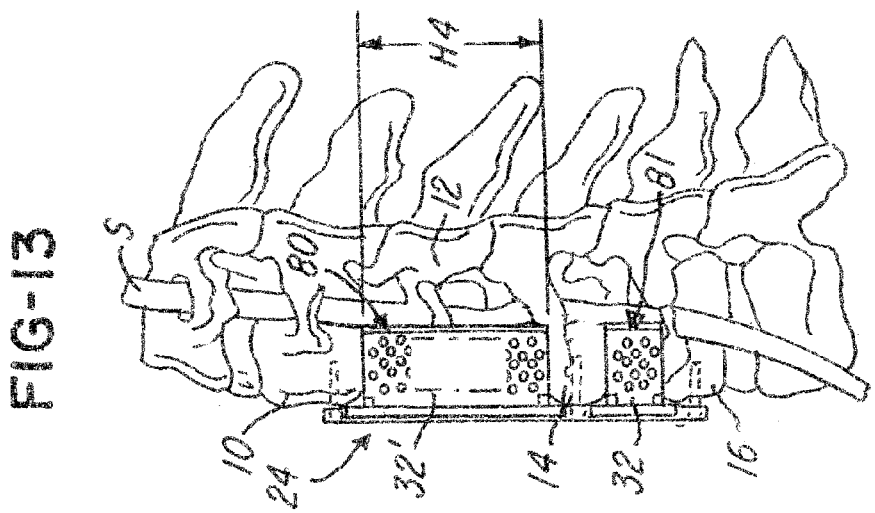

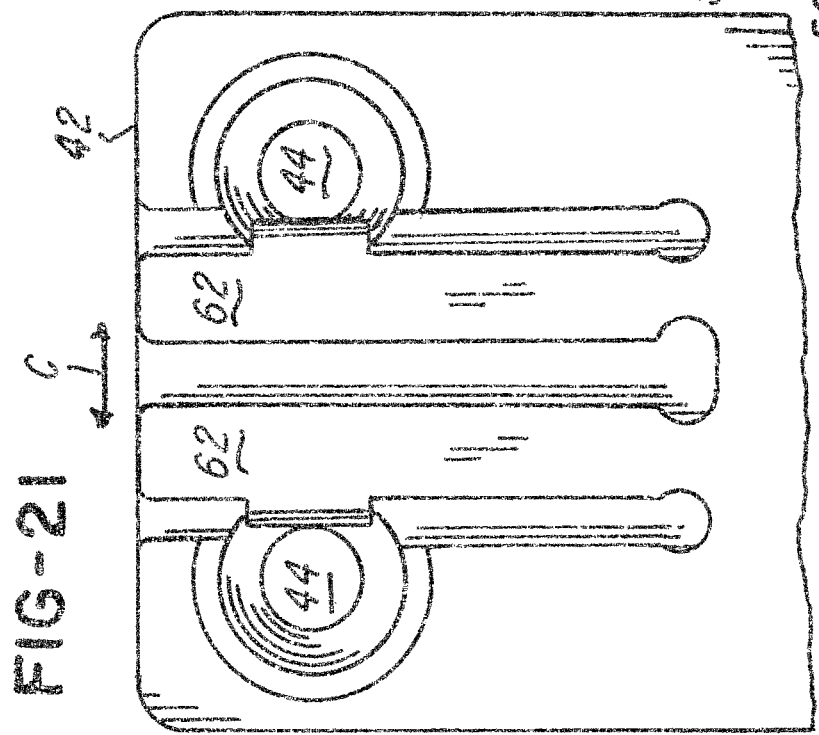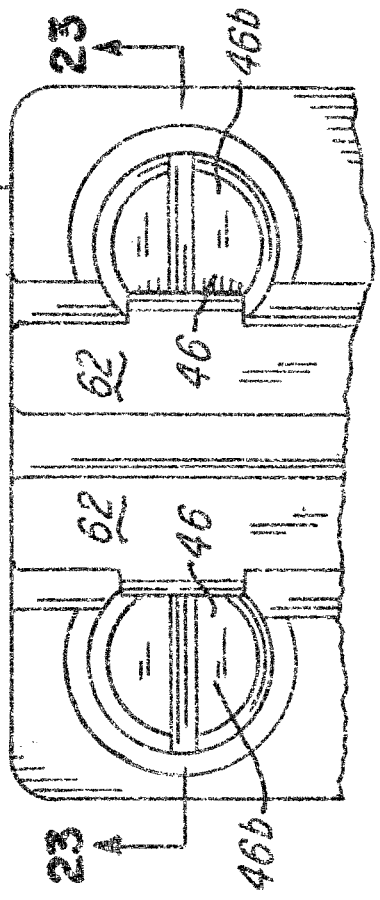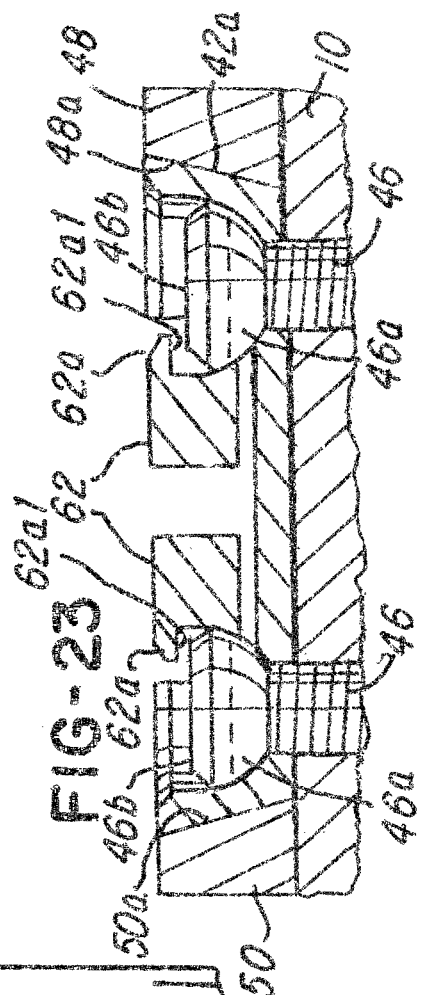

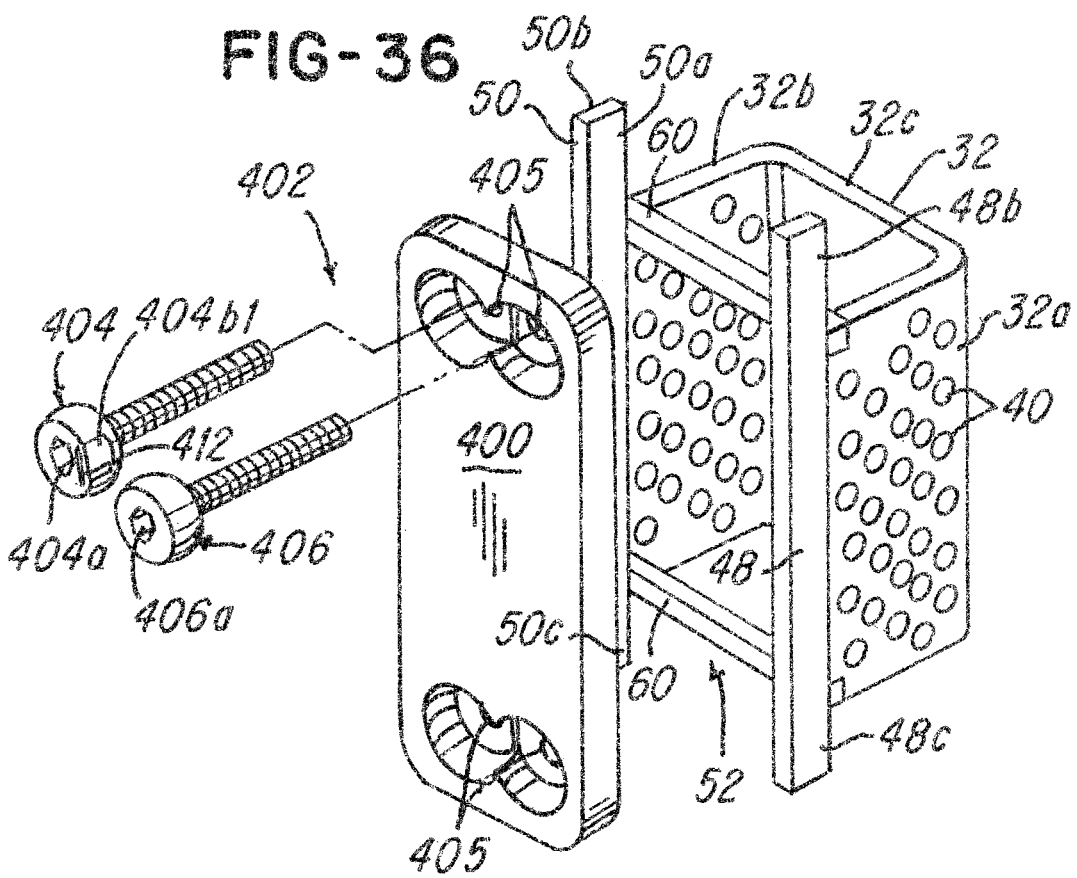
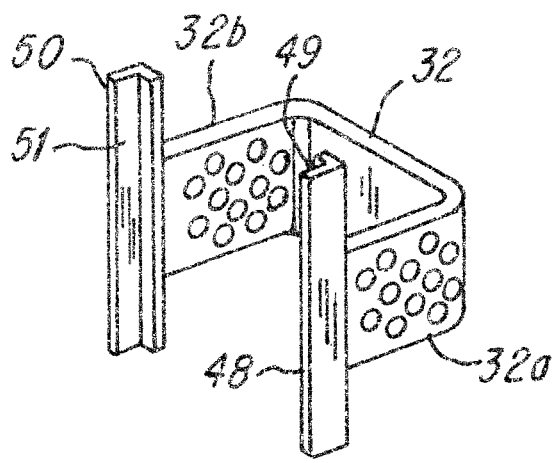

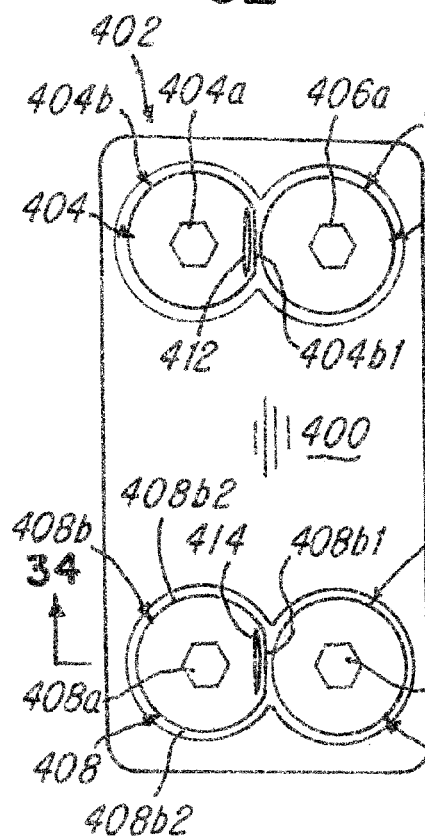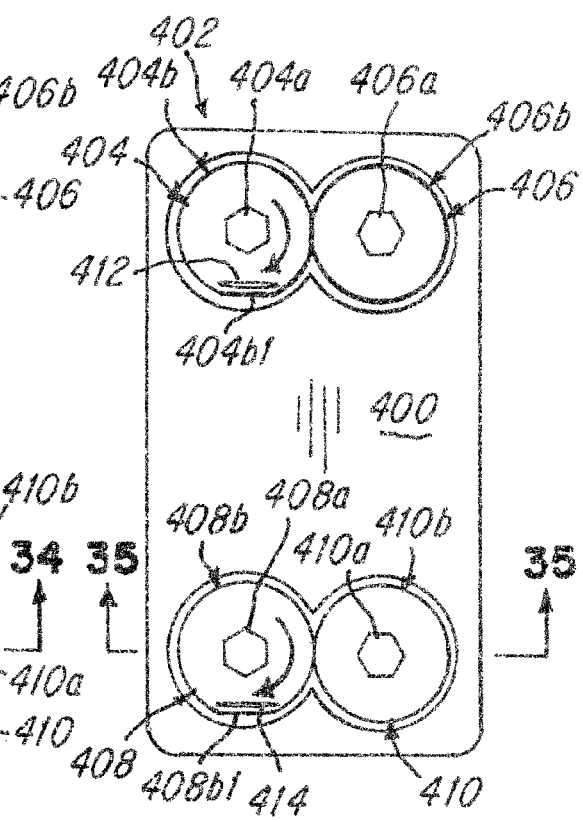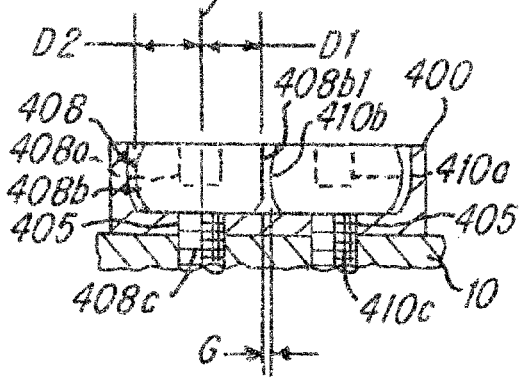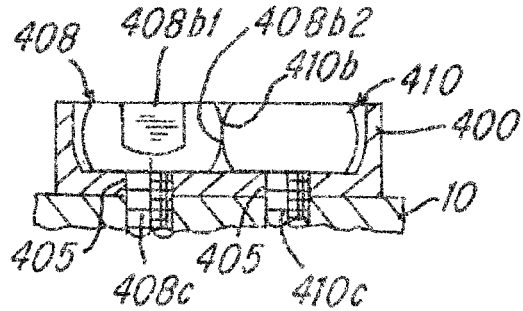

FUSION SYSTEM AND METHOD FOR FUSING SPINAL BONES

RELATED APPLICATION DATA

This application is a continuation of U.S. patent application Ser. No. 12/640,061, filed Dec. 17, 2009 which is a continuation-in-part of Ser. No. 11/624,341 filed Jan. 18, 2007, now issued as U.S. Pat. No. 7,655,028, which is a division of U.S. patent application Ser. No. 10/675,361, filed Sep. 30, 2003, now issued as U.S. Pat. No. 7,182,782, all of which are incorporated herein by reference and made a part hereof. This application is also a continuation of U.S. patent application Ser. No. 10/858,629, filed Jun. 2, 2004, now issued as U.S. Pat. No. 7,641,701, which is a continuation-in-part of U.S. patent application Ser. No. 10/675,361, filed Sep. 30, 2003, now issued as U.S. Pat. No. 7,182,782, all of which are incorporated herein by reference and made a part hereof.

BACKGROUND OF THE INVENTION

1. Field of the Invention

This invention relates to a veritable prosthetic system and device and a method for implanting the device and, more particularly, to a spinal fusion system and method for fusing spinal bones.

2. Description of the Related Art

Many types of prosthetic devices have been proposed in the past. For example, U.S. Pat. No. 5,192,327 to Brantagan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 5,192,327; 5,261,911; 5,713,899; 5,776,196; 6,136,002; 6,159,245; 6,224,602; 6,258,089; 6,261,586; 6,264,655; 6,306,136; 6,328,738 and 6,592,586. Some or all of these devices have improved the success rate and have simplified the surgical techniques in inter-body veritable fusion.

Among some of the problems associated with the prior art devices is that after the device is inserted into a patient during a surgical procedure, there was a possibility of retropulsion of the inter-body device and graft material into the spinal cord or other neurological element.

Another problem with the prior art devices is that grafting material, which was inserted into the devices during the surgical procedure, could not easily be inserted from an anterior direction.

Moreover, in some of the prior art devices, the cover, if any, was typically fastened directly to the device and to spinal bones, which prevented the cover from being capable of moving relative to the device. In addition, in devices that used a cover, the cover did not function to both retain the grafting material in the device and simultaneously fix the spinal bones relative to each other.

Another problem with prior art cage systems is that the screws or fasteners which secured the cover onto the cages sometimes had a tendency to unscrew themselves which is undesirable because the graft material may exit the cage or because the cage itself may move. Another problem is that the screws may withdraw, causing injury to local structures by the screws themselves.

What is needed, therefore, is a system and method, which facilitates overcoming one or more of the aforementioned problems as well as other problems and to provide a device that has unique features that will facilitate reducing the risk associated with neurological surgeries and advance the present state of the art.

SUMMARY OF THE INVENTION

It is, therefore, one object of the invention to provide a spinal fusion system and method which utilizes a housing that can be inserted, but comprises features which, for example, enables the device to float relative to a cover, facilitates retaining any graft material within the device, facilitates fixing a relative relation among or between spinal bones, facilitates providing a cover for covering one or multiple devices, and/or includes locking features that facilitates preventing the screws which secure the cover to the spinal bones from the retracting.

Another object of one embodiment is to provide a plurality of screws that are capable of locking to facilitate preventing the fasteners to become unfastened or unscrewed.

Another object of the invention is to provide fasteners at least one of which has an eccentric to facilitate locking against an adjacent fastener in order to retain the fasteners and the cover in a locked position.

In one aspect, this invention comprises an apparatus for surgical use in humans, comprising a housing for insertion between vertebrae in a human spine, a recess in the housing for receiving bone graft material, a cover securable to at least one of the adjacent vertebrae and being configured to block egress of the bone graft material from the recess, and the cover and the housing being slidably engaged one to the other.

In another aspect, the invention comprises a surgical implant, comprising a housing, a recess in the housing for receiving bone graft material, the housing having an opening in a side thereof, the opening communicating with the recess and being configured for insertion of the bone graft material into the recess, a cover mechanically engaging the housing so as to permit sliding relative movement therebetween, the cover being configured to retain the bone graft material within the recess.

In yet another aspect, the invention comprises a surgical implant for use with human vertebrae, comprising: a generally U-shaped housing defining an opening in an anterior side thereof, a recess in the housing communicating with the opening, the recess being configured for receiving bone graft material, and a cover in locating and mating engagement with the housing, the cover being securable to at least one of the adjacent vertebrae and configured to block egress of the bone graft material from the recess.

In still another aspect, the invention comprises a surgical implant for use with human vertebrae, comprising: a generally U-shaped housing having a plurality of closed sides and an open side defining an opening at an anterior of the housing, the housing being disposable between adjacent vertebrae, a recess in the housing communicating with the opening, the recess extending through superior and inferior portions of the housing and being configured for receiving bone graft material therein, a cover mechanically coupled with the housing so as to permit sliding relative movement therebetween, the cover being disposed over the opening and configured to block egress of the bone graft material from the recess with the cover being securable to at least one of the adjacent vertebrae, and screw-receiving apertures in the cover for accommodating screws securing the cover to the at least one adjacent vertebrae.

In yet another aspect, the invention comprises a method for fusing spinal bones together, comprising the steps of: removing diseased or injured spinal bones and/or vertebral disks, and situating a spinal implant between remaining spinal bones, the spinal implant comprising a housing, a recess in the housing having bone graft material therein and a cover secured to at least one of the remaining spinal bones, the cover blocking egress of the bone graft material from the recess and the cover and the housing being slidably engaged one to the other.

In still another aspect, the invention comprises a method for fusing spinal bones together, comprising the steps of: removing diseased or injured spinal bones and/or vertebral disks, and situating a spinal implant between remaining spinal bones, the spinal implant comprising a generally U-shaped housing having an opening in an anterior side thereof, a recess in the housing having bone graft material therein, and a cover secured to at least one of the remaining spinal bones, the cover blocking egress of the bone graft material from the recess and the cover and being in locating and mating engagement with the housing.

These and other objects and advantages of the invention will be apparent from the following description, the accompanying drawing and the appended claims.

BRIEF DESCRIPTION OF THE DRAWINGS

FIG. 1 is a partial side view of a human spine illustrating anteriorly discs between various spinal bones;

FIG. 2 is a partial side view of the spinal column shown in FIG. 1 illustrating several of the discs removed, for example, after surgical procedure;

FIG. 3 is a partial side view of the human spine with the housings according to one embodiment of the invention situated therein;

FIG. 7 is an exploded view of the device shown in FIG. 6, illustrating a plurality of housings and a single cover for use with covering the plurality of housings;

FIG. 8 is partial side view illustrating an elongated housing and cover used during a vertebrectomy procedure;

FIG. 9 is a partial side view of the spinal column illustrated in FIG. 8 showing the elongated housing situated between adjacent spinal bones in a single cover to be affixed to those spinal bones;

FIG. 10 is an exploded view of the circle area shown in FIG. 8;

FIG. 11 is a exploded view of the elongated housing illustrated in FIGS. 8 and 9 and the cover and screws associated therewith;

FIG. 12 is a partial fragmentary view of the cover and housing after the cover has been situated between a pair of rails associated with the housing;

FIG. 13 illustrates a partial side view of an embodiment showing a plurality of housings of different sizes used with a single cover;

FIG. 14 is an exploded view of the housings and cover illustrated in FIG. 13;

FIG. 21 is a fragmentary view illustrating various features of the cover;

FIG. 22 is another fragmentary view of the cover after the screws are mounted and the locking mechanism retains the screws therein;

FIG. 23 is a fragmentary sectional view of the embodiment shown in FIG. 22 illustrating various features of the locking mechanism;

FIG. 31 is a view of a housing having walls having recessed areas for receiving the cover;

FIG. 32 is a view of another embodiment of the invention showing the plurality of fasteners or screws in an unlocked position;

FIG. 33 is a view of the fasteners or screws shown in FIG. 32 in a locked position;

FIG. 34 is a view taken along the line 34-34 in FIG. 32;

FIG. 35 is a view taken along the line 35-35 in FIG. 33; and

FIG. 36 is an exploded view of the other embodiment of the invention with the locking screws illustrated in FIGS. 32-35.

DETAILED DESCRIPTION OF PREFERRED EMBODIMENTS

Figure 6:
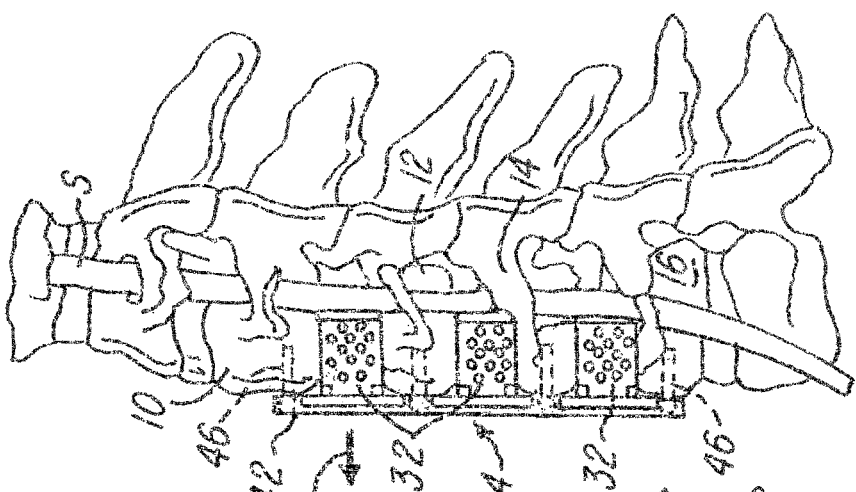
FIG. 6 is a side view similar to FIG. 5 illustrating after the cover has been mounted to the spinal column.

Referring now to FIG. 1, a partial side view of a patient or person P is shown having a spinal column S and a plurality of spinal bones, such as vertebrae, 10, 12, 14 and 16. Note that a disc, such as discs 18, 20 and 22 in FIG. 1, is located between adjacent pairs of spinal bones (e.g., between bones 10 and 12, 12 and 14, and 14 and 16). During a spinal fusion procedure, such as a discectomy, the discs 18, 20 and 22 may be removed so that adjacent vertebrae may be fused together FIG. 2 illustrates a fragmentary view of the spinal column S shown in FIG. 1, with the discs 18, 20 and 22 removed. It should also be understood that during another surgical procedure, such as a vertebrectomy, it may be desired to remove part or all of one of the spinal bones 10-16, as illustrated in FIG. 13. In this type of neurological procedure, it may also be desired to fuse adjacent spinal bones together for reasons that are conventionally known. This invention provides means for facilitating and performing such procedures. For ease of illustration, FIGS. 15-20 provide corresponding anterior views to the side views shown in FIGS. 1-6, respectively.

In the embodiment being described, a spinal fusion system 24 is provided for use as a prosthetic implant during a neurological procedure such as the aforementioned vertebrectomy or discectomy. In general, after the discs 18, 20 and 22 (FIG. 1) are removed, as illustrated in FIG. 2, a plurality of receiving areas 26, 28 and 30 (FIGS. 2 and 17) are defined by the areas between the surfaces of adjacent spinal bones 10, 12, 14 and 16. As illustrated in FIG. 2, the area 26 is bounded in part by the surface 10a of spinal bone 10 and surface 12a of spinal bone 12. Likewise, area 28 is partially bounded by surface 12b of spinal bone 12 and surface 14a of spinal bone 14, and area 30 is bounded by surface 14b of spinal bone 14 and surface 16a of spinal bone 16.

Figure 4:
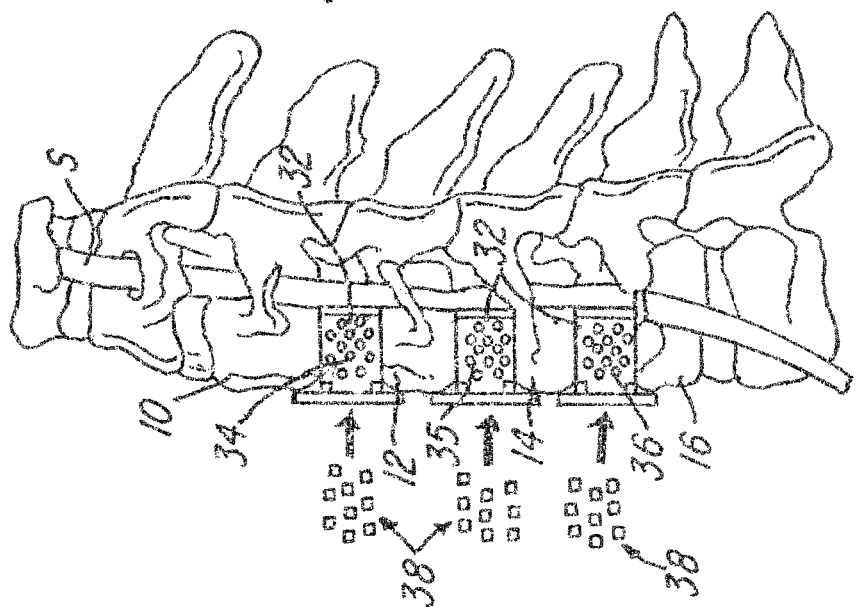
FIG. 4 is a partial side view of the human spinal column illustrating graft material being inserted anteriorly into the housing.

As illustrated in FIGS. 3-7 and 11 and as will be described in more detail later herein, the spinal fusion system 24 comprises a housing 32 dimensioned to be situated or received between adjacent spinal bones, such as bones 10 and 12. A housing 32 is situated in each of the plurality of receiving areas 26, 28 and 30, as illustrated in FIGS. 3-4. Each housing 32 cooperates with adjacent spinal bones to define a graft area, such as areas 34, 35 and 36 in the view illustrated in FIG. 17, for receiving graft material 38 (FIGS. 4 and 18). As illustrated in FIGS. 4 and 18, the graft material 38 is situated in the areas 34, 35 and 36 after placement of the housing 32.

As illustrated in FIG. 11, the housing 32 is generally U-shaped as shown. In the embodiment being described, the housing 32 comprises a well 33 defining multiple sides and comprising a predetermined shape selected to cause the graft material to be formed into a multi-sided fused coupling between adjacent spinal bones, such as bones 10 and 12 in FIG. 3. Although not shown, the housing 32 could define a shape other than rectangular, such as semi-circular, oval or other suitable shape as may be desired. Note that the housing 32 comprises a first wall 32a, a second wall 32b and a third wall 32c joining the first wall 32a and the second wall 32b. One or more of the walls 32a-32c may comprise a plurality of holes or apertures 40 which facilitate the fusing process. The apertures 40 also permit visualization of graft material 38 on x-rays.

As mentioned later herein, the predetermined shape defined by the spinal fusion system 24 may provide a fused multi-sided plug of fusion material 38 having a height H (FIGS. 14 and 16) of at least two millimeters, but typically less than approximately 180 millimeters. This height H may vary depending on the vertical size or height H (as viewed in FIG. 16) of the areas 26-30 to be filled. For example, in the area 26 illustrated in FIGS. 2, 14 and 16, the height H of the area 26 generally corresponds to a height H1 (FIG. 1) of a disc, such as disc 18. Thus, the fusion material 38 (FIG. 18) would resultantly have a fused height H2 (FIG. 18) that generally corresponds to the height H (FIG. 16) and height H1 (FIG. 1). If, for example, a housing 32 having a longer height is required, such as height H3 in FIG. 14 and height H4 in FIG. 13, such as in the event of a vertebrectomy, then the fusion system 24 and housing 32 will define a height that generally corresponds to the dimension or height H (FIG. 9) to be traversed. Thus, it should be understood that the dimensions of the generally U-shaped housing 32 of the spinal fusion system 24 is selected depending on the size of the area 26-30 to be filled and the environment or application in which the spinal fusion system 24 is used. In general, the width and depth of the housing 32 will be approximately 9-20 millimeters and 7-20 millimeters, respectively.

Figure 5:
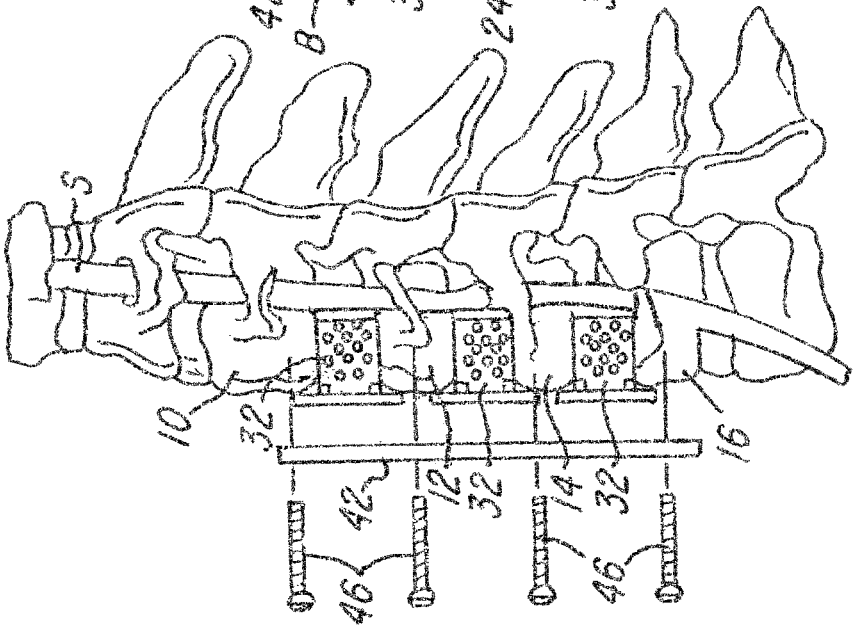
FIG. 5 is a partial exploded side view of the embodiment shown in FIG. 1-4 illustrating a cover and a plurality of screws which will secure the cover to the spinal column.

As illustrated in FIGS. 5-7, 11, 14 and 21-22, the spinal fusion system 24 further comprises a cover 42 comprising a plurality of apertures 44 that receive a plurality of screws 46, respectively, which are screwed directly into the spinal bones 10 and 16, as illustrated, for example, in FIGS. 5-6.

Figure 20:
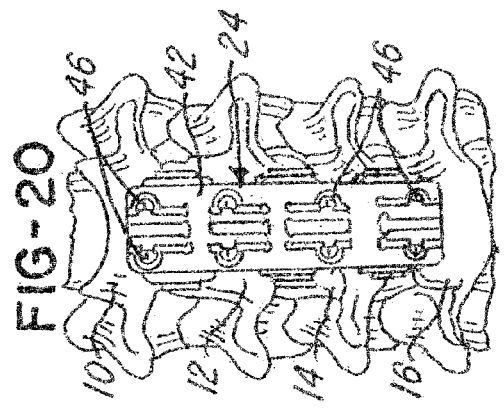
FIG. 20 is a anterior view similar to FIG. 5 illustrating the cover mounted to the spinal column.

As illustrated in FIG. 11, the housing 32 comprises a first rail, channel wall or wall portion 48 and a second rail, channel wall or wall portion 50 which cooperate to define a channel area 52 for receiving the cover 42. It should be understood that when the cover 42 is received in the channel area 52, the sides 42a and 42b become associated with the sides 48a and 50a. It should be understood that the cover 42 is not permanently secured to the housing 32 after it is received in channel area 52. This feature permits the housing 32 to migrate or float relative to the cover 42 even after the cover 42 is fixed to one or more of the spinal bones 10-16 as illustrated in FIGS. 6 and 20. As illustrated in FIG. 23, the edges 42a and 42b of cover 42 and sides 48a and 50a may be beveled and complementary to facilitate locating and mating engagement between the cover 42 and housing 32.

Figure 19:
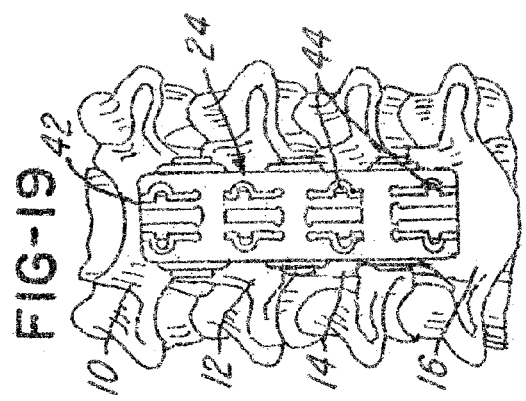
FIG. 19 is a partial exploded anterior view of the embodiment shown in FIG. 1-4 illustrating a cover and a plurality of screws for securing the cover to the spinal column.

As illustrated in FIGS. 3-6 and 16-20, after the graft material 38 is placed in the housing 32 and the graft areas 35-36 (FIG. 17) defined by the housing 32 and adjacent spinal bones, then the cover 42 is situated between the walls or rails 48 and 50, as illustrated in FIGS. 6 and 19. The screws 46 may then be used to secure the cover 42 to one or more of the spinal bones 10-16 as illustrated in FIGS. 6 and 20. It should be understood that a feature of the invention is that the cover 42 facilitates aligning the housings 32 in a substantially co-lineal or relatively aligned position relative to each other and to the spinal bones 10-16, as illustrated in FIGS. 6, 19 and 20. In the setting of multiple level discectomy, the floating cover 42 allows limited, controlled settling of the cages or housings 32 in the vertical plane with respect to the cover 42. As illustrated in FIGS. 6, 8, 10 and 20, the cover 42 also provides means for providing a mechanical fixation of the adjacent spinal bones 10-16 relative to each other. Thus, while the housing 32 cooperates with adjacent spinal bones, such as spinal bones 10 and 12, to define a graft receiving area 34, the cover is multi-functional in that it not only covers the opening of any graft areas, such as area 34 (FIG. 17), but it also secures and retains the spinal bones 10-16 in a fixed spatial relationship relative to each other and relative to the housings 32. It should also be understood that the cover 42 may be fixed to one or more of the spinal bones 10-16 as may be desired to accomplish either of the aforementioned functions.

As illustrated in FIG. 11, note that the walls 48 and 50 further define projections 48b, 48c, 50b and 50c as shown. As illustrated in FIGS. 3-6 and 17-20, the projections 48b, 48c, 50b and 50c provide a plurality of migration preventers for preventing the housing 32 from migrating posteriorly in the direction of arrow A (FIG. 3) toward the spinal cord S or other neurological elements after the housing 32 is situated between the adjacent spinal bones 10-16 as illustrated. Further, the migration preventers 48b, 48c, 50b and 50c enable a surgeon to locate each housing 32 between adjacent spinal bones, such as spinal bones 10-16 in FIG. 1, and move the housing 32 in the direction of arrow A in FIG. 3 until the migration preventers 48b, 48c, 50b and 50c engage the surface 10a of spinal bone 10 and migration preventers 48b, 48c, 50b and 50c engage the surface 12a of spinal bone 12. As illustrated in FIG. 3, after the housings 32 are situated between the spinal bones 10-16 as shown, the migration preventers 48b, 48c, 50b and 50c facilitate preventing the wall 32c from being over-inserted by the surgeon or from being over-inserted to a point where it engages the spinal cord S or other neurological elements.

Figure 26:
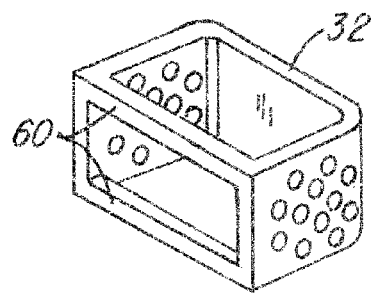
FIG. 26 is a view of another embodiment of the invention showing the crossbars integrally formed in the housing and without migration preventers.

The spinal fusion system 24 further comprises at least one migration stop or crossbar 60 as illustrated in FIGS. 11, 12, 29 and 30. The crossbar 60 may be either integrally formed in housing 32, as shown in FIG. 26, or separate as illustrated in FIGS. 7, 11, 12, 14, 29 and 30, for example. As illustrated in the exploded view in FIGS. 10 and 11, the surface 60a of crossbar 60 engages and cooperates with surface 42c of cover 42 to prevent anterior migration in the direction of arrow B). Thus, the spinal fusion system 24 of the embodiment being described provides means for preventing insertion of the housing 32 to a point where it might engage the spinal cord S (FIG. 3) or other neurological elements, such as dura mater, thecal sac, and also means for facilitating prevention of migration of the housing 32 in an anterior direction or in the direction of arrow B in FIG. 10 after the housing 32 is situated as described herein and the cover 42 is mounted to one or more of the spinal bones 10-16.

Figure 29:
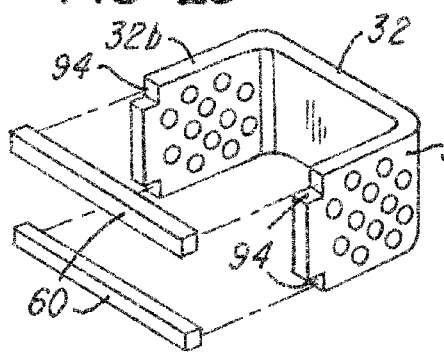
FIG. 29 is another view of the housing illustrating a plurality of removable crossbars without any migration preventers.
Figure 30:
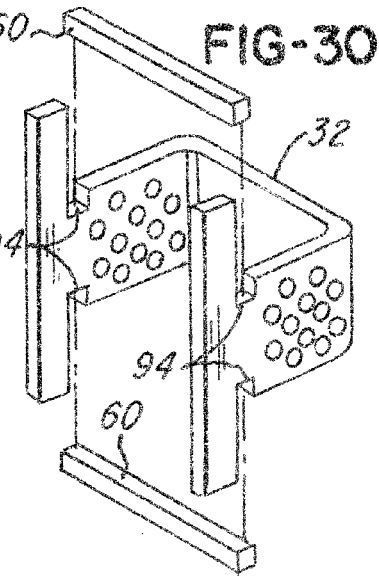
FIG. 30 illustrates another embodiment of the invention, similar to the devices illustrated earlier relative to FIG. 1-20 showing details of the cross bars and notches for receiving them.

It should be understood that a plurality of the migration stops or cross bars 60 may be used alone or in combination with the migration preventers 48b, 48c, 50b and 50c. It should be understood that the stops 60 could be detachable, as shown in FIG. 26, or they could be integrally formed in housing 32 (as shown in FIG. 26). Also, these cross bars 60 may be removably received in the notched receiving areas 94 (FIGS. 29-30). For example, in anatomy that provided limited space, the surgeon may elect not to use a housing with cross bars 60 or use a housing that does not have integrally formed cross bars.

The system 24 further comprises a system or means for preventing retraction or back out of the screws 46 after they are screwed into the spinal bones 10-16 in order to secure the cover 42 thereto. The spinal fusion system 24 of the present invention may be used with conventional screw lock devices or with a unique locking mechanism and system, which will now be described relative to FIGS. 21-23.

As illustrated in FIGS. 21-23, the spinal fusion system 24 and, more particularly, cover 42 may be provided with at least one or a plurality of resilient detents 62 which are generally L-shaped as shown and are resilient so that they can move laterally in the direction of double arrow C in FIGS. 21-22 towards and away from a home position (FIG. 21) to permit the screws 46 first received in the apertures 44, and, second, locked into the cover 42. Thereafter, the screws 46 may be screwed into a spinal bone, such as spinal bone 10, and when a screw head 46a of the screw 46 engages a detent portion 62a of the resilient detent 62, the resilient detent 62 moves in a direction away from the apertures 44 until the screw head 46a clears the portion 62a. After a top surface 46b of the screw head 46a has cleared the bottom surface 62a1 (as viewed in FIG. 23) of portion 62a, the resilient detent 62 moves back toward aperture 44 to the home position until the portion 62a and surface 62a1 are operatively positioned over surface 46b of screw 46, thereby retaining and preventing the screws 46 from backing out of the cover 42 and thereby preventing the screws 46 from backing out of the spinal bone 10.

The plate comprises a first surface 50d (FIG. 23) and a second surface 50e. The plate member further comprises a seat or edge 50f (FIG. 21) associated with the first surface 50d and the detent 62a associated with the second surface 50e.

In the embodiment being described, the components of the spinal fusion system 24, such as the housing 32, first channel wall portion 48 and second channel wall portion 50, crossbar 60, cover 42 and screws 46 may be made of any desired composition or material such as a polymer, composite polymer, titanium, stainless steel, carbon fiber or other suitable material.

Figure 15:
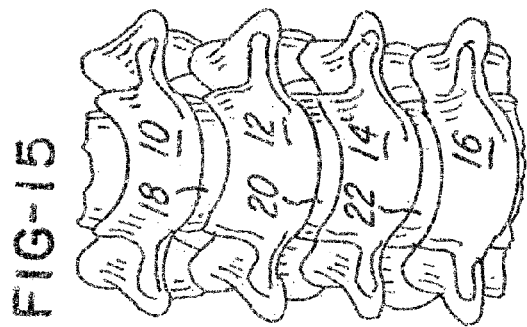
FIG. 15 is a partial anterior side view a human spine illustrating the discs between various spinal bones.

A method for fusing spinal bones together will now be described relative to FIG. 22. It should be understood that this procedure may be used during a vertebrectomy or discectomy or other neurological procedure during which it is desired to fuse spinal bones together. For ease of illustration, the embodiment will be described as used during a discectomy procedure during which the discs 18-22 (FIG. 1) are removed so that spinal bones 10-16 may be fused together. The procedure begins by situating a patient P on an operating table (not shown) and providing an appropriate incision as conventionally known to expose the spinal bones such as the bones 10-16 illustrated in the side view shown in FIG. 1 and in the anterior view illustrated in FIG. 15. (Block 70 in FIG. 22). At Block 72, the vertebrae or discs, such as discs 18-22 in FIGS. 1 and 15, are surgically removed revealing the areas 26-30 in FIGS. 2 and 16. At Block 74, the housings 32 are inserted in the direction of arrow A (FIG. 3) into the areas 26, 28 and 30 until the migration preventers 40b, 48c, 50b and 50c engage the surfaces of the spinal bones 10-16, such as the surfaces 10a and 12a illustrated in FIG. 3. (Block 74 in FIG. 22). As mentioned earlier herein, the migration preventers facilitate preventing inserting the housing 32 to a point which would cause the wall 32c to engage the spinal column S.

Figure 17:
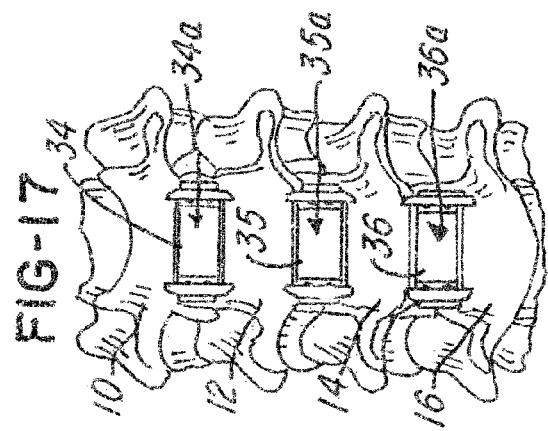
FIG. 17 is a partial anterior view of the human spine with the housings according to one embodiment of the invention situated therein.
Figure 16:
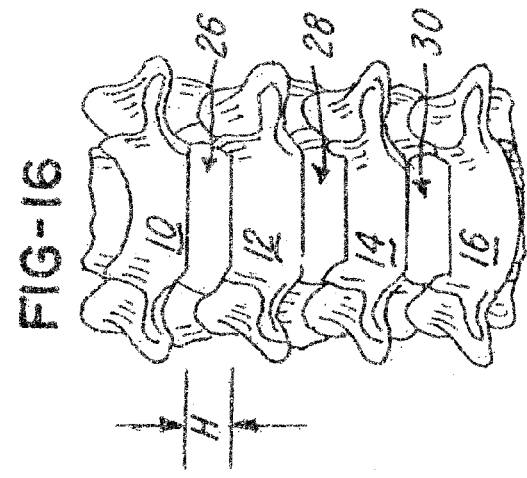
FIG. 16 is a partial anterior view of the spinal column shown in FIG. 1 illustrating several of the discs removed, such as by surgical procedure.
Figure 18:
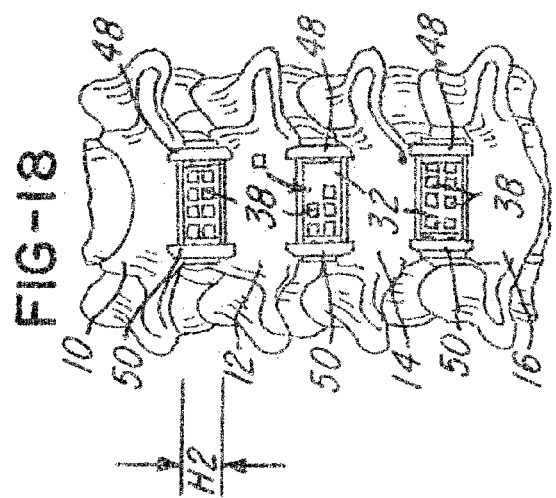
FIG. 18 is a partial anterior view of the human spinal column illustrating graft material being inserted anteriorly into the housing.

As illustrated in FIGS. 3 and 17, the housing 32 cooperates with adjacent spinal bones, such as bones 10 and 12 to define the graft receiving area or cavity 34 in which the graft material 38 (FIG. 4) may be inserted. As mentioned earlier herein, these graft areas 34-36 may comprise a shape which is generally rectangular, as defined by the shape of the housing 32, but it could comprise another shape by simply providing a housing 32 having a different predetermined shape. Thus, the housing 32 may be provided in a circular or arcuate shape in which case the graft area 34 would define a generally circular or arcuate area, which would cause the graft material to form a similar shape. Other curved or multi-sided shapes may be defined by providing an appropriately or correspondingly shaped housing 32, depending on the selected or desired shape that the physician would like the fused graft material 38 to assume after it has fused to the adjacent spinal bones.

At Block 76, the graft material 38 is inserted and at Block 78, the cover 42 is situated in the slot or area 52 defined by the walls 48 and 50. As mentioned earlier herein, the cover 42 facilitates covering the openings, such as openings 34a and 36a of the graft areas 34 and 36, respectively. The surgeon secures the cover 42 to one or more of the bones, as illustrated in FIGS. 5-6 and 19-20 and then closes the patient (Block 80).

Figure 24:
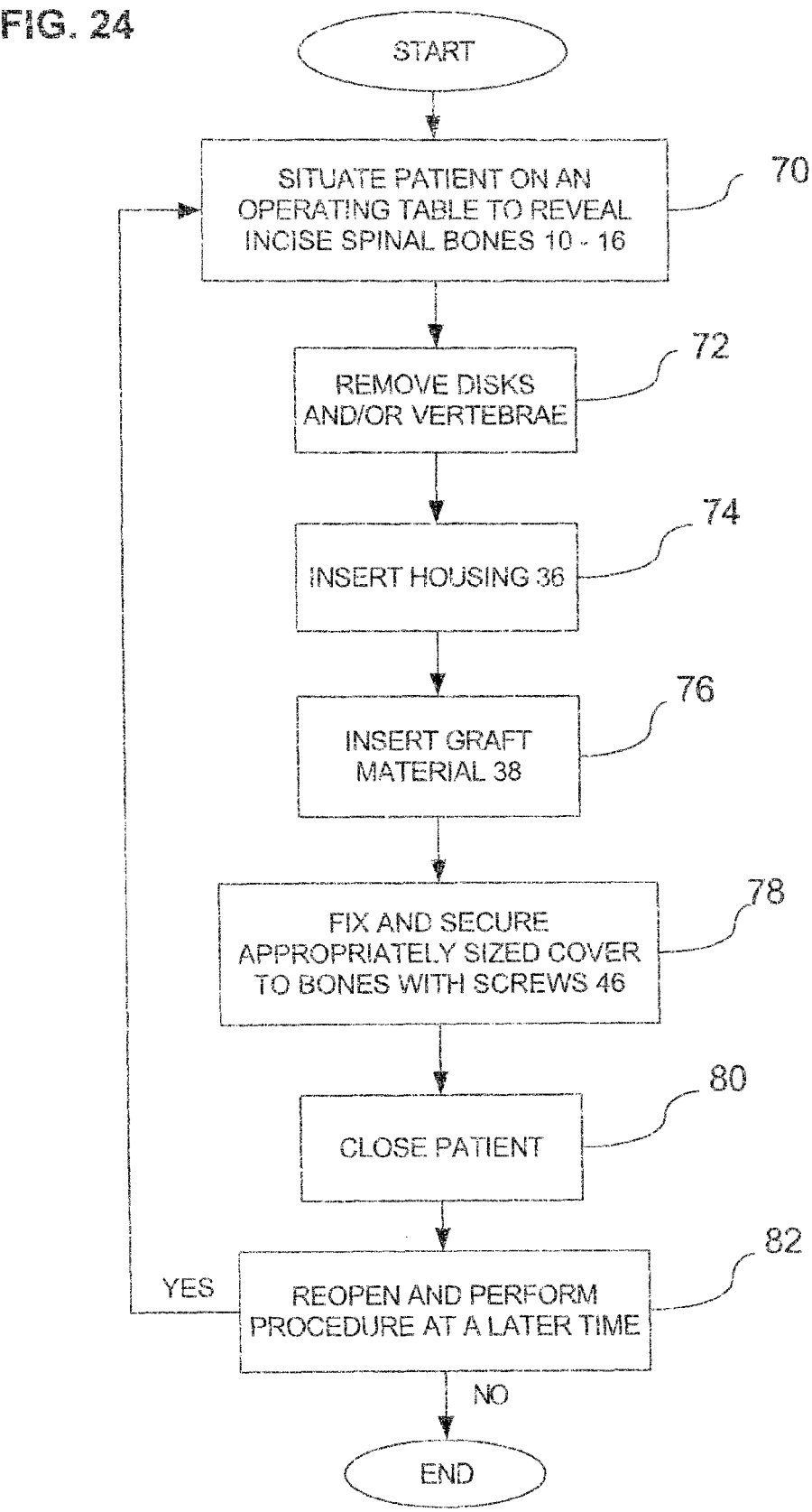
FIG. 24 is a schematic view of a process or method in accordance with an embodiment of the invention.

Again, and as mentioned earlier, a feature of the invention is that it provides a fixing system for fixing the location of the bones 12-16 relative to each other. Simultaneously, the system 24 permits the housing 32 to "float" between adjacent bones, such as bones 10 and 12 in FIGS. 3 and 6. This is advantageous for reasons mentioned earlier herein. Another advantage on this feature of the invention is that if it is necessary to operate on the same patient at a later time (Block 82 in FIG. 24) and, for example, add one or more housings 32 in order to fuse other spinal bones together, then the cover 42 can simply be removed at a later time, another discectomy or vertebrectomy performed and another housing 32 inserted. Another cover 42, or perhaps a second cover may then be used to seal the additional housing 32 after it is situated in the manner described herein. Thus, this invention provides a system and method, which is flexible and will permit the addition or insertion of additional housings 32 of the same or different sizes during a second operating procedure as illustrated in Block 82.

FIGS. 1-8 and 15-20 illustrate the general procedure and use of the invention in an illustrative discectomy wherein three discs are removed, replaced with housing 32, and graft material 38 inserted as described, and cover 42 situated and mounted as described herein. In the illustration shown in FIGS. 1-8 and 15-20, three discs 18-22 are removed and the spinal bones 12-16 are fused together using the system and method as shown and described. It should be appreciated, however, that this system and method may be used with fewer or more housings 32 and with one or a plurality of covers 42 as may be desired or required. For example, if only one of the discs 18-22 needed to be excised and only two of the spinal bones 10-16 fused together, then only one housing 32 and cover 42 may be necessary. Likewise, as mentioned earlier herein, the housings 32 may comprise a different dimension or different height H (FIG. 14) to span a greater area, such as the area H4 illustrated in FIGS. 13 and 14. For example, FIGS. 13 and 14 illustrate a vertebrectomy wherein the spinal bone 12 has been removed along with the disc between spinal bones 14 and 16. This provides areas 80 and 81 in which an elongated housing 32', such as the housing 32' illustrated in FIG. 14 may be inserted. After the housings 32 and 32' are inserted between the spinal bones 10-14 and 14-16 as shown in FIG. 13, graft areas 82 and 84 are provided for receiving the graft material 38. As illustrated in FIG. 13, the cover 42 would have a corresponding elongated shape for fixing the bones 10 and 14 together and for covering both openings 82 and 84 or housings 32 and 32'.

It is also anticipated that the invention may be used in a multitude of procedures, such as a vertebrectomy (FIGS. 8 and 9), discectomy (FIGS. 1-7, 13-20, or even a combination of a vertebrectomy and discectomy as illustrated in FIGS. 13-14. As mentioned and described earlier herein, a combination of different sizes of housings 32 and covers 42 may be used as shown. Although it is preferred that a single cover 42 be used, it may be desired in some applications to use multiple covers 42, such as where the removed discs are not adjacent.

In the illustrations being described, the housings 32 comprise the crossbar 60 which cooperate with the cover 42 to prevent anterior migration of the housing after the screws 46 are secured to the spinal bones as illustrated in FIGS. 6, 9 and 13.

Figure 25:
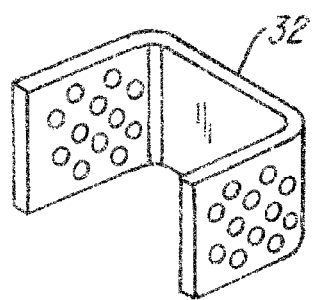
FIG. 25 illustrates another embodiment of the invention without crossbars or migration preventers.

FIGS. 25-30 illustrate other embodiments of the invention. In FIG. 25, a generally U-shaped housing 32 is provided without the walls 48 and 50 or crossbar 60. This embodiment may be useful. This may be useful if it were desired to insert housing 32 in local anatomy so that it could be loaded from the side or laterally, rather than anteriorly, as previously described.

In FIG. 26 a housing 32''' is provided with the crossbars 60, but without the walls 48 and 50. In this embodiment it may be useful to use such a housing design when the local anatomy provides limited space.

Figure 27:
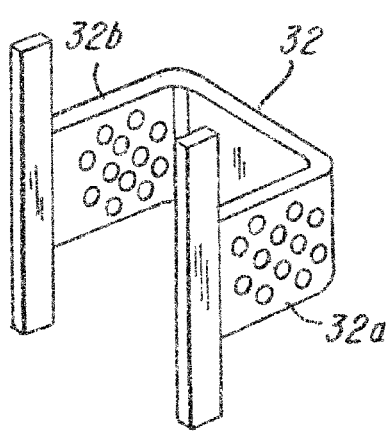
FIG. 27 is a view illustrating a plurality of migration preventers, without any crossbars.
Figure 28:
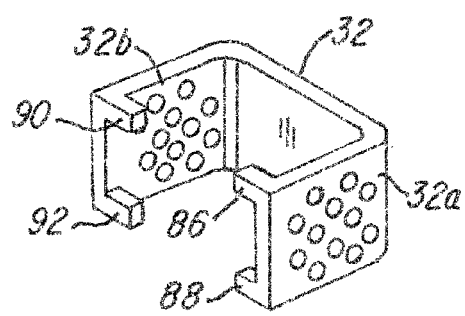
FIG. 28 is a view illustrating a housing with a plurality of projections which cooperate with the cover to prevent the housing from migrating anteriorly.

FIG. 27 illustrates yet another embodiment of the invention illustrating a housing 32 that is provided with a plurality of protrusion 86, 88, 90 and 92 that do not span completely between the walls 32b or 32a together but yet provide the protrusions 86-92 which will engage the cover 42 if the housing attempts to migrate anteriorly as described earlier herein. FIGS. 1-24, 29 and 30 show embodiments of the invention where the crossbars 60 are not integrally formed with the housing 32, but received in the notched areas 94 as shown. As mentioned earlier, the crossbars 60 may be separate or may be integrally provided with the housing 32. Providing detachable crossbars 60, such as is shown in the embodiments illustrated in FIGS. 25, 28 and 29, enable the walls 32a and 32b to flex towards and away from each other. The housing 32 may be provided with a malleable material in which case the surgeon can change the general U-shape of the housing 32 to accommodate the size or shape of the areas 34 and 36 (FIG. 17). In the embodiment described, housing 32 and cover 42 may be made of titanium, polymer or a bioresorbable material.

FIG. 31 illustrates the walls 48 and 50 having notched areas 49 and 51 for receiving the cover 42 which is dimensioned to fit, thereby eliminating the need for cross bars 60.

FIGS. 32-36 illustrate another embodiment of the invention. In this embodiment, those parts that are the same or similar to the parts illustrated in FIGS. 1-30 are identified with the same part number, except that the parts in FIGS. 31-36 have an apostrophe ("''") mark added thereto.

In this embodiment, the cage system 24 comprises a cover 400 for situating in the channel area 52 (FIG. 11) to facilitate preventing interior migration of the graft material 38. In order to secure the cover 400 over the graft area 34 or 36, a locking system, means and method are provided for retaining the cover 400 on the housing 32. In the embodiment being described, the locking system 402 comprises a plurality of screws, fastening means or fasteners 404, 406, 408 and 410 that are received in openings, such as openings 405 in the cover plate 400 as shown. Note that the fasteners 404-410 comprise a plurality of female openings or slots 404a, 406a, 408a and 410a for receiving a tool, such as a hex wrench for tightening and loosening the fasteners 404-410.

In the embodiment being described, the fasteners 404 and 408 comprise a head 404b and 408b that have a planar or flat portion 404b1 and 408b1 as shown. As best illustrated in FIGS. 34 and 35, note that the fasteners 408 and 410 each comprise threads or a threaded portion, such as threads or portions 408c and 410c of fasteners 408 and 410, respectively. Note that a distance or small radius D1 between center C1 and flat portion 408b1 in FIG. 34 is smaller than the distance or large radius D2 measured by the distance between center C1 and wall 408b2 in FIG. 35. The difference in the distances D1 and D2 facilitates defining a cam surface or lobe on the wall 408b2 whose use and purpose will be defined later herein.

In the embodiment being described, one or more of the heads 404b, 406b, 408b and 410b may comprise an indicia, such as a grind mark or other indicator 412 and 414 (FIG. 32), to facilitate and assist a user, such as a doctor, to identify the small radius portion D1 during a surgical procedure. Thus, the indicia 412 and 414 facilitate defining the surface associated with the flat portion, such as portion 404b1.

It should be understood that when the pairs of fasteners 404-406 and 408-410 are aligned such that the flat portion 404b1 and 408b1 and short or small radius portion D1 are situated in opposite or closest to wall 406b of screw 406 and wall 410b of screw 410 the adjacent fasteners 406 and 410 respectively, may be rotated and screwed into, for example, vertebrae 10, which will secure and retain the cover 400 over the graft area 34 or 36. Although not shown, the locking system of the present invention may comprise eccentric fasteners of screws having eccentric heads (i.e. where a head center is offset from a thread axis) and fasteners that are used with non-eccentric fasteners. For example, and as illustrated in FIG. 33, fasteners 404 and 408 may comprise the aforementioned eccentric, while adjacent fasteners 406 and 410, respectively, may be non-eccentric fasteners or screws.

In any event, the small radius portion D1 permits the adjacent fastener or screw such as screw 410, whether it has an eccentric or not, to be turned when the small radius portion D1 or flat portion 408b1 is situated in opposed relationship to the adjacent screw (as illustrated in FIGS. 32 and 34). For example, FIG. 34 illustrates that when the fasteners are aligned such that the indicia 414 are aligned as illustrated in FIG. 32, a gap G exists between the portions 408d1 and wall 410d of screw 410 as shown. The gap G permits either or both of the fasteners 408 and 410 to rotate in either a counterclockwise or clockwise direction during fastening and unfastening of the fasteners to the vertebrae as described earlier herein with the prior embodiments.

When it is desired to secure the cover 400 over the housing 32, the fasteners 404-408 are placed in the cover and aligned as illustrated in FIG. 32. The fasteners 404-408 are rotated and screwed into vertebrae 10 in a clockwise direction until it is seated. These fasteners 404 and 408 are then "backed out" less than a full turn until flat surface 404b1 and 408b1 are aligned as shown in FIG. 32. The surgeon may use the indicator 412 and 414 to perform this alignment. This alignment presents the gap G (FIG. 34), which permits the fastener 410 to be rotated in a clockwise direction until completely screwed into vertebrae 10.

Next, the adjacent fastener (406 for the 404-406 pair and 410 for the 408-410 pair) is inserted into opening 405 in cover 400 and in FIGS. 32 and 34 until they are fully seated into the vertebrae 10. For example, in the illustration shown in FIGS. 32 and 34, the fastener 408 is rotated in a clockwise direction with a tool, such a hex wrench (not shown) until it is fully seated into the vertebrae 10.

The fastener 408 is again rotated in the clockwise direction (as viewed) until the large radius portion D2 and the wall portion 408b2 engages and comes against the wall 410b of the fastener 410.

It should be appreciated that when the fasteners 404-410 are secured in the locked position in the manner described, they facilitate retaining themselves in the locked position. For example, if fastener 410 begins to rotate in a counterclockwise direction (as viewed in FIG. 33) it will cause fastener 408 to rotate in a clockwise direction which, in turn, causes fastener 408 to tighten and resist the counterclockwise rotation of fastener 410. If fastener 410 would rotate, fastener 408 would screw deeper into the vertebrae 10.

FIG. 36 is an illustration similar to FIG. 11 showing the orientation and alignment of the cover 400 and fasteners 404-410 to the housing 32.

Advantageously, the various embodiments of the invention illustrated in FIG. 1, provide a system and method for inserting graft material 38 into a graft area 34 and 36 (FIG. 17) to fuse a plurality of bones such as bones 10-18 together. The system and method also provide means for fixing the bones 10-18 relative to each other, while permitting the housing 32 to cooperate with adjacent bones 10-18 to define a graft area 34 and 36 (FIG. 17) and to also float relative to the cover 42. The locking system illustrated in FIGS. 21-23 further facilitates providing a locking system that does not require the use of any tools, yet prevents back out of the screws 46.

While the apparatus and method described constitute preferred embodiments of this invention, it is to be understood that the invention is not limited to this precise apparatus and method, and that changes may be made in either without departing from the scope of the invention, which is defined in the appended claims.

What is claimed is:

1. An apparatus for surgical use in humans, comprising:
    a housing for insertion between adjacent vertebrae in a human spine, said housing having a plurality of closed sides and an open side defining an opening;
    a recess in said housing for receiving bone graft material, said recess communicating with said opening;
    a cover configured to be secured to at least one of the adjacent vertebrae; and
    said cover and said housing being slidably engaged one to the other.

2. The apparatus of claim 1 wherein said housing is generally U-shaped.

3. The apparatus of claim 1 wherein said open side is located at an anterior of said housing.

4. The apparatus of claim 1 wherein one or more of said closed sides includes a plurality of apertures formed therethrough.

5. The apparatus of claim 1 wherein said cover is securable to each of the adjacent vertebrae.

6. The apparatus of claim 1 wherein said cover is configured to block egress of said housing from between the adjacent vertebrae.

7. The apparatus of claim 1 wherein said cover includes screw-receiving apertures for accommodating screws securing said cover to the at least one adjacent vertebrae.

8. The apparatus of claim 7 further comprising screws disposed in said apertures.

9. The apparatus of claim 1 further comprising bone graft material in said recess.

10. A surgical implant, comprising:
    a housing for insertion between adjacent vertebrae in a human spine, said housing having a plurality of closed sides and an open side defining an opening;
    a recess in said housing for receiving bone graft material, said recess communicating with said opening; and
    a cover configured to be secured to at least one of the adjacent vertebrae and mechanically engaging said housing so as to permit sliding relative movement therebetween, said cover being configured to retain bone graft material within said recess.

11. The surgical implant of claim 10 wherein said housing is generally U-shaped.

12. The surgical implant of claim 10 wherein said housing is usable as an intervertebral implant and disposable between adjacent vertebrae, said cover being securable to at least one of the adjacent vertebrae.

13. The surgical implant of claim 12 wherein said cover is securable to each of the adjacent vertebrae.

14. The surgical implant of claim 10 wherein said cover is disposed over said opening and is moveable independently of said housing.

15. The surgical implant of claim 12 wherein said cover includes screw-receiving apertures for accommodating screws securing said cover to the at least one adjacent vertebrae.

16. The surgical implant of claim 15 further comprising screws disposed in said apertures.

17. The surgical implant of claim 10 further comprising bone graft material in said recess.

18. A surgical implant for use with human vertebrae, comprising:
    a generally U-shaped housing for insertion between adjacent vertebrae in a human spine, said housing defining an opening in an anterior side thereof;
    a recess in said housing communicating with said opening, said recess being configured for receiving bone graft material; and
    a cover in locating and mating engagement with said housing, said cover being configured to be secured to at least one of the adjacent vertebrae.

19. The surgical implant of claim 18 wherein said cover is securable to each of the adjacent vertebrae.

20. The surgical implant of claim 18 wherein said cover is disposed over said opening and is moveable independently of said housing.

21. The surgical implant of claim 18 wherein said cover includes screw-receiving apertures for accommodating screws securing said cover to the at least one adjacent vertebrae.

22. The surgical implant of claim 21 further comprising screws disposed in said apertures.

23. The surgical implant of claim 18 further comprising bone graft material in said recess.

24. A surgical implant for use with human vertebrae, comprising:
a housing having a plurality of closed sides and an open side defining an opening at an anterior of said housing, said housing being disposable between adjacent vertebrae of a human spine;
a recess in said housing communicating with said opening, said recess extending through superior and inferior portions of said housing;
a cover mechanically coupled with said housing so as to permit sliding relative movement therebetween, said cover being disposed over said opening with said cover being configured to be secured to at least one of the adjacent vertebrae; and
screw-receiving apertures in said cover for accommodating screws securing said cover to the at least one adjacent vertebrae.

25. A method for fusing spinal bones together, comprising the steps of:
removing diseased or injured spinal bones and/or vertebral disks; and
situating a spinal implant between remaining spinal bones, the spinal implant comprising a housing having a plurality of closed sides and an open side defining an opening, a recess in the housing communicating with the opening and having bone graft material therein, and a cover secured to at least one of the remaining spinal bones, the cover and the housing being slidably engaged one to the other.

26. The method of claim 25, further comprising the step of:
blocking egress of the housing from between the remaining spinal bones with the cover.

27. A method for fusing spinal bones together, comprising the steps of:
removing diseased or injured spinal bones and/or vertebral disks; and
situating a spinal implant between remaining spinal bones, the spinal implant comprising a generally U-shaped housing having an opening in an anterior side thereof, a recess in the housing having bone graft material therein, and a cover secured to at least one of the remaining spinal bones, the cover being in locating and mating engagement with the housing.

28. The method of claim 27, further comprising the step of:
blocking egress of the housing from between the remaining spinal bones with the cover.

29. The surgical implant of claim 24 wherein said housing is U-shaped.

30. An apparatus for surgical use in humans, comprising:
a generally U-shaped housing for insertion between adjacent vertebrae in a human spine, said housing defining an opening and having at least one wall including a channel;
a recess in said housing communicating with said opening;
a cover configured to be secured to at least one of the adjacent vertebrae; and
said cover being in locating and mating engagement with said housing when at least a portion of said cover is received in said channel.

31. The apparatus of claim 30 wherein said housing has a pair of walls each including a respective channel.

32. The apparatus of claim 30 wherein said cover is securable to each of the adjacent vertebrae.

33. The apparatus of claim 30 wherein said cover includes screw-receiving apertures for accommodating screws securing said cover to the at least one adjacent vertebrae.

34. The apparatus of claim 33 further comprising screws disposed in said apertures.

35. A surgical implant, comprising:
a generally U-shaped housing for insertion between adjacent vertebrae of a human spine, said housing defining an opening and having at least one wall including a channel;
a recess in said housing, said opening communicating with said recess; and
a cover configured to be secured to at least one of the adjacent vertebrae and being in locating and mating engagement with said housing when at least a portion of said cover is received in said channel.

36. The surgical device of claim 35 wherein said housing has a pair of walls each including a respective channel.

37. The surgical implant of claim 35 wherein said opening is at an anterior of said housing.

38. The surgical implant of claim 35 wherein said housing is usable as an intervertebral implant and disposable between adjacent vertebrae, said cover being securable to at least one of the adjacent vertebrae.

39. The surgical implant of claim 36 wherein said cover is securable to each of the adjacent vertebrae.

40. The surgical implant of claim 36 wherein said cover includes screw-receiving apertures for accommodating screws securing said cover to the at least one adjacent vertebrae.

41. The surgical implant of claim 37 further comprising screws disposed in said apertures.

42. An apparatus for surgical use in humans, comprising:
a housing for insertion between adjacent vertebrae in a human spine, said housing having a plurality of closed sides and an open side defining an opening;
a recess in said housing for receiving bone graft material, said recess communicating with said opening; and
a cover configured to be secured to the adjacent vertebrae, said cover and said housing each being discrete and engaged one to the other.

43. The apparatus of claim 42 wherein said housing is generally U-shaped.

44. The apparatus of claim 42 wherein said open side is located at an anterior of said housing.

45. The apparatus of claim 42 wherein one or more of said closed sides includes a plurality of apertures formed therethrough.

46. The apparatus of claim 42 wherein said cover is securable to each of the adjacent vertebrae.

47. The apparatus of claim 42 wherein said cover includes screw-receiving apertures for accommodating screws securing said cover to the at least one adjacent vertebrae.

48. The apparatus of claim 47 further comprising screws disposed in said apertures.

49. The apparatus of claim 42 further comprising bone graft material in said recess.

50. A surgical implant for use with human vertebrae, comprising:
- a generally U-shaped housing for insertion between adjacent vertebrae in a human spine, said housing defining an opening in an anterior side thereof;
- a recess in said housing communicating with said opening, said recess being configured for receiving bone graft material; and
- a cover having screw-receiving apertures for accommodating screws configured to secure said cover to the adjacent vertebrae,
- said cover and said housing being discrete and engaged one to the other.

51. The surgical implant of claim 50 further comprising screws disposed in said apertures.

52. The surgical implant of claim 50 further comprising bone graft material in said recess.

53. A method for fusing spinal bones together, comprising the steps of:
- removing diseased or injured spinal bones and/or vertebral disks; and
- situating a spinal implant between remaining spinal bones, the spinal implant comprising a housing having a plurality of closed sides and an open side defining an opening, a recess in the housing communicating with the opening and having bone graft material therein, and a cover secured to at least one of the remaining spinal bones, the cover and the housing being discrete and engaged one to the other.

54. The method of claim 53, further comprising the step of: blocking egress of the housing from between the remaining spinal bones with the cover.

55. The method of claim 53 wherein the housing is U-shaped.

* * * * *